United States Patent [19]
Wyttenbach

[11] Patent Number: 5,795,289
[45] Date of Patent: Aug. 18, 1998

[54] SPECULUM

[76] Inventor: William H. Wyttenbach, 6905 Sunset Ave., Panama City Beach, Fla. 32327

[21] Appl. No.: 901,619

[22] Filed: Jul. 28, 1997

[51] Int. Cl.$^6$ .................................................. A61M 29/02
[52] U.S. Cl. ........................... 600/207; 606/193; 606/198
[58] Field of Search ..................... 606/198, 119, 606/193, 192; 600/207, 184, 195, 203

[56] References Cited

U.S. PATENT DOCUMENTS

| | | |
|---|---|---|
| 2,548,602 | 4/1951 | Greenburg . |
| 3,044,461 | 7/1962 | Murdock . |
| 3,774,596 | 11/1973 | Cook . |
| 4,899,729 | 2/1990 | Gill et al. ........................... 606/198 X |
| 5,197,971 | 3/1993 | Bonutti ................................. 606/192 |
| 5,316,023 | 5/1994 | Palmaz et al. ........................ 128/898 |
| 5,328,469 | 7/1994 | Coletti ................................. 604/96 |
| 5,460,170 | 10/1995 | Hammerslag .......................... 600/201 |
| 5,484,499 | 1/1996 | Amundson et al. ................... 606/108 |
| 5,674,240 | 10/1997 | Bonutti et al. ....................... 606/198 |

*Primary Examiner*—Michael H. Thaler
*Attorney, Agent, or Firm*—Peter Loffler

[57] ABSTRACT

A speculum is comprised of a shaft member having a cavity passing therethrough and an outer layer and an inner layer with a bladder, capable of holding a bio-acceptable liquid, disposed therebetween. At least one guide member runs along the lateral length of the shaft member within the cavity. An end cap is attached to one end of the shaft member and an expansion cap is rotatably received within the end cap. A coil spring has one end attached to one of the at least one guide members proximate the distal end of the shaft member and the opposing end attached to the expansion cap. Rotation of the expansion cap into the end cap causes lateral length reduction of the spring which increases coil diameter and thus shaft member diameter and thereby increases the lumen of the device. Counter-rotation of the expansion cap out of the end cap causes coil turn and shaft member diameter reduction.

6 Claims, 4 Drawing Sheets

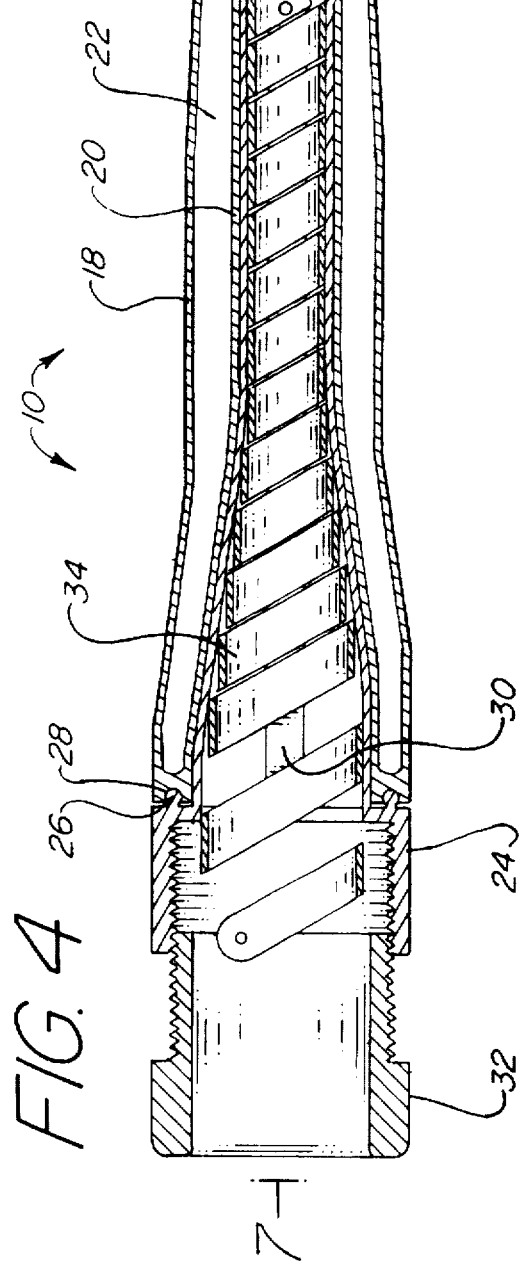
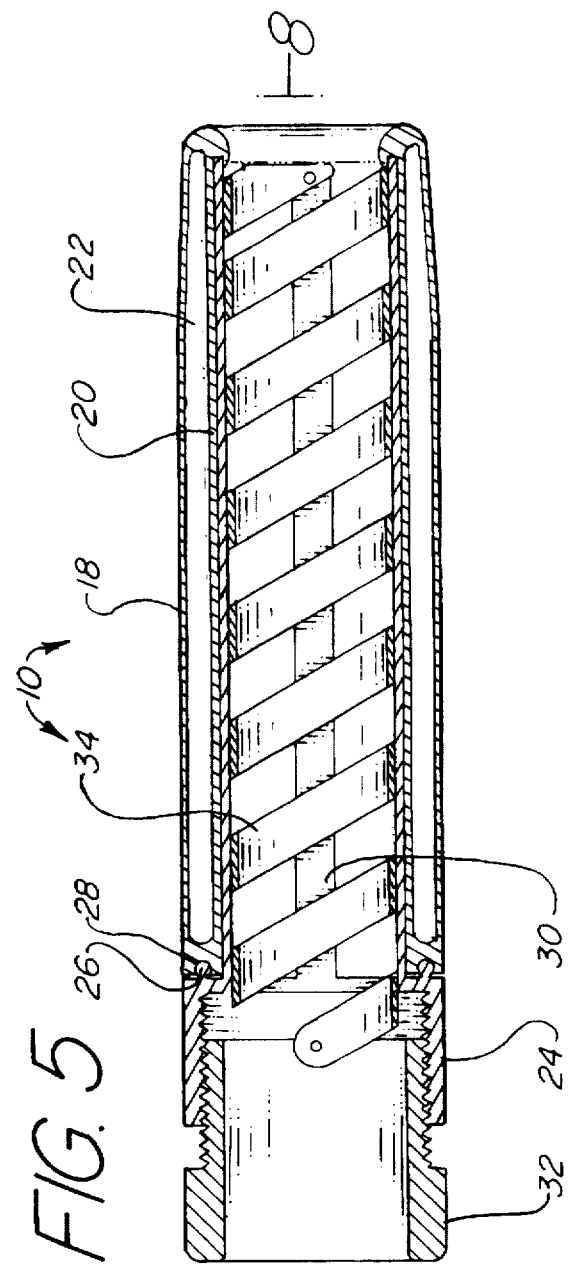

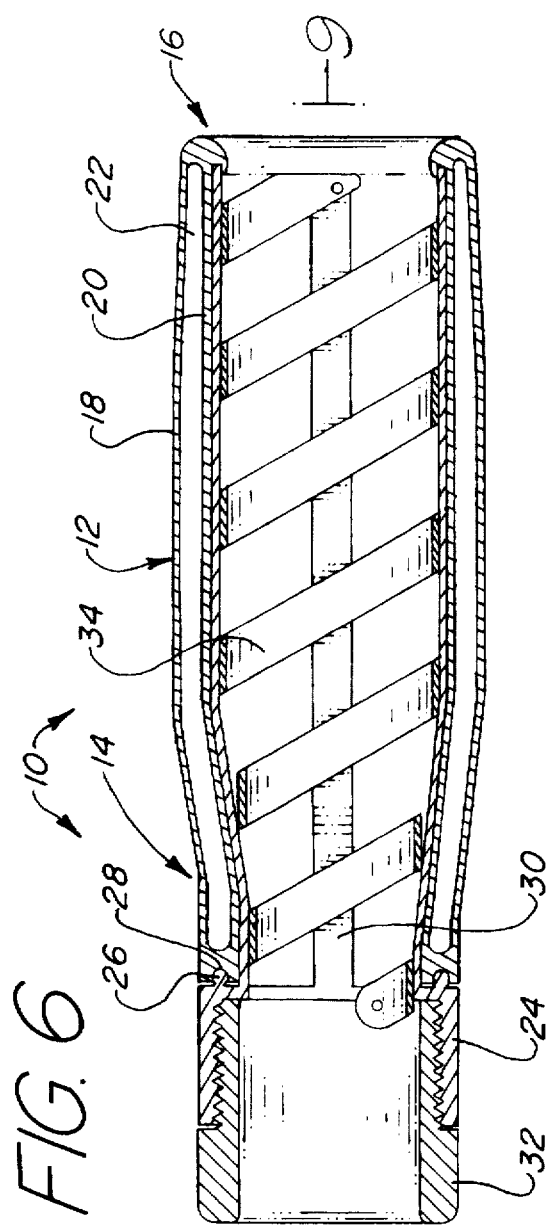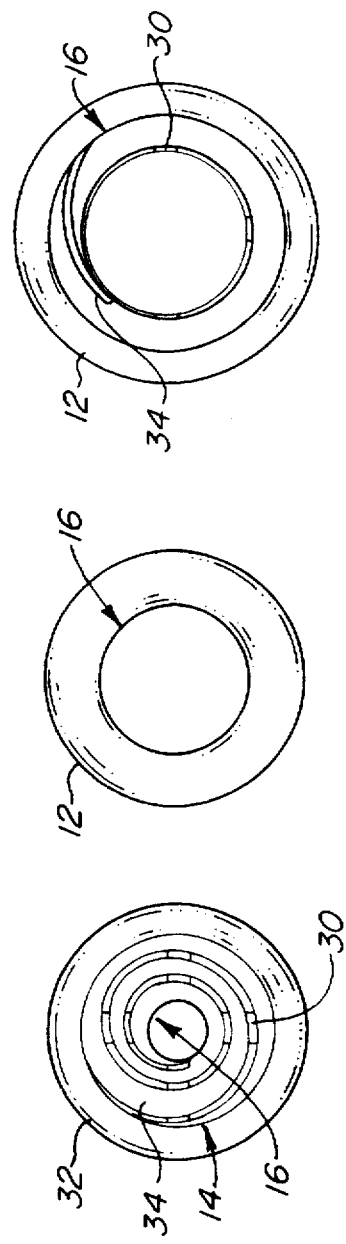

SPECULUM

BACKGROUND OF THE INVENTION

1. Field of the Invention

The present invention relates to a device, usable for a female vaginal examination, having an expandable lumen.

2. Background of the Prior Art

In performing a female vaginal-pelvic examination, the medical practitioner must gain visual access into the vaginal canal in order to properly view the female anatomy and, if necessary, to obtain a viral or bacterial culture therefrom or to perform a routine pap smear from the cervix. Typically, an expansion device is used that has a "duck-bill" or "vice-like" action that is inserted into the vagina and is expanded in order to open the vagina for medical examination. Such devices, which are typically fabricated from metal or hard plastic, have a tendency to pinch or otherwise uncomfortably stretch the delicate vaginal walls of the female patient. Furthermore, these devices, as a result of their material makeup, tend to be relatively cold to the patient adding to the discomfort of the examination.

As such an examination is difficult at best for the female patient, the use of medical implements that increase the physical discomfort to the patient, only add to the overall negative experience gained from such an examination. However, as such examinations are an integral component of a female's physical medical maintenance, most patients will undergo the requisite physical discomforts associated with such an examination.

There is, therefore, a need in the art for a device that will substantially reduce, if not eliminate, the physical discomforts associated with a typical female vaginal-pelvic medical examination. Such a device should eliminate the pinching and tearing of the delicate vaginal walls. The device should not pose a substantial temperature differential to the female patient. The device must permit the medical practitioner to perform a proper visual, and if necessary bacterial or viral culture examination of the female anatomy or to perform a routine pap smear. Ideally, such a device should be of relatively simple and straightforward design and construction and should not be unduly burdensome to use.

SUMMARY OF THE INVENTION

The speculum of the present invention addresses the aforementioned needs in the art. The speculum greatly reduces the physical discomforts to the female patient during a typical vaginal-pelvic examination, yet permits the medical practitioner to properly perform the examination without undue difficulty.

The speculum of the present invention is comprised of a shaft member having a lateral central cavity passing therethrough and having an outer layer and an inner layer defining a bladder therebetween. The bladder is capable of receiving a liquid, heated or unheated, therein. The outer layer and the inner layer are each constructed from an expansive resilient material. An end cap is attached to the proximal end of the shaft member. At least one guide member is attached to the end cap and extends along the length of the shaft member terminating proximate the distal end. An expansion cap is rotatably received within the end cap. One end of a spring is attached to the expansion cap while the opposing end is attached to one of the guide members proximate the distal end. Rotation of the expansion cap into the end cap causes a decrease in the number of coil turns of the spring which causes an increase in the diameter of each coil turn. This causes an expansion of the shaft member and its cavity. Reversal of the process causes a reduction in shaft member and cavity diameter.

The device has a relatively small diametrical footprint upon insertion into the female patient. Once properly inserted, the device is gently and gradually expanded so as to eliminate the painful pinching and uncomfortable stretching of the vaginal wall. Filling the bladder with an appropriate warmed liquid adds to the physical comfort associated with the device.

The device permits a full and proper female anatomical exam without undue physical discomfort to the female patient. The device gives the medical practitioner appropriate visual and physical access. The gently expanding nature of the device, coupled with the warm liquid filled bladder, give the female patient a relatively warm and comfortable feeling during the examination. Furthermore, the device overcomes the common problem of the prior art of the collapse of the lateral vaginal walls into the field of examination in obese or morbidly obese patients.

The device is of relatively simple and straightforward construction and is easy to use in operation. The device may be disposable, or may be reusable upon proper sterilization and with the use of an appropriate disposable sleeve.

BRIEF DESCRIPTION OF THE DRAWINGS

FIG. 4 is a cutaway view of the speculum of the present invention in its initial state.

FIG. 5 is a cutaway view of the speculum in an expanded state.

FIG. 6 is a cutaway view of the speculum in its fully expanded state.

FIG. 7 is a rotated end view of FIG. 4.

FIG. 8 is a rotated end view of FIG. 5.

FIG. 9 is a rotated end view of FIG. 6.

Similar reference numerals refer to similar parts throughout the several views of the drawings.

DESCRIPTION OF THE PREFERRED EMBODIMENT

Figure 1:
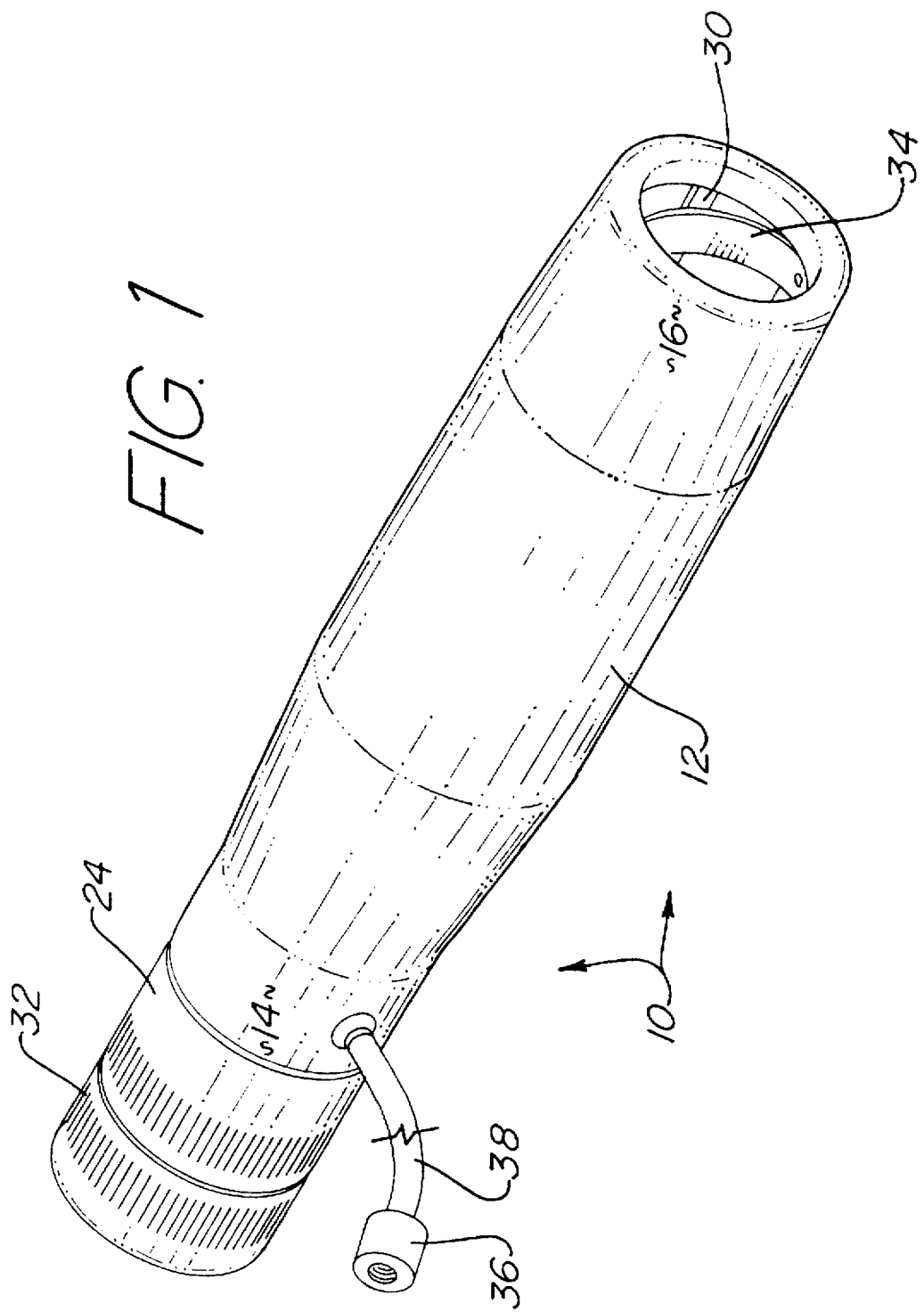
FIG. 1 is a perspective view of the speculum of the present invention.
Figure 2:
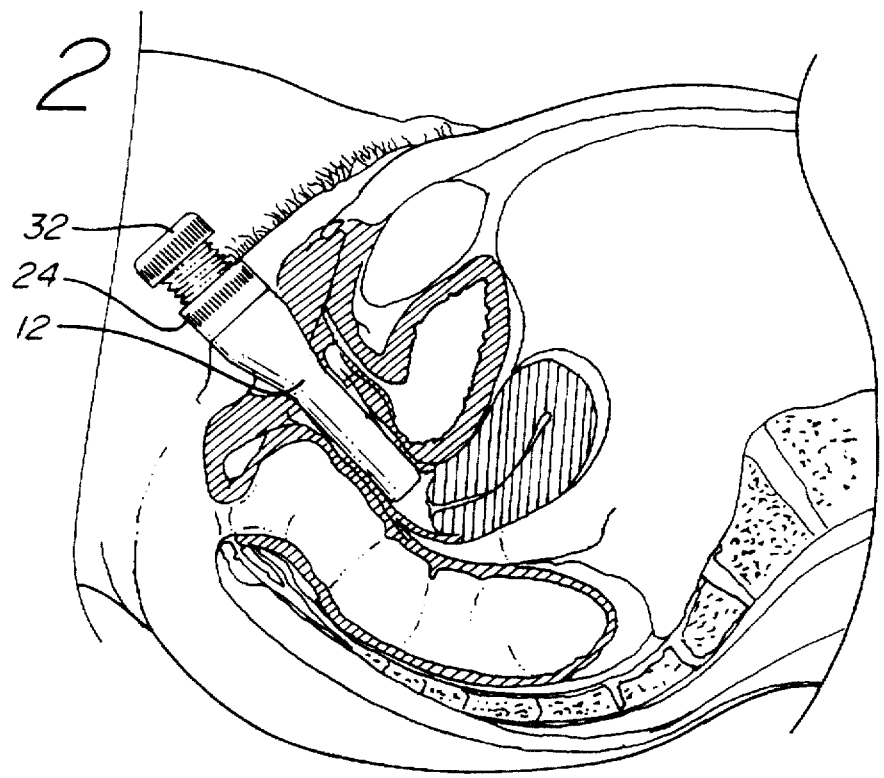
FIG. 2 is an illustration of the speculum upon initial insertion into the female vagina.
Figure 3:
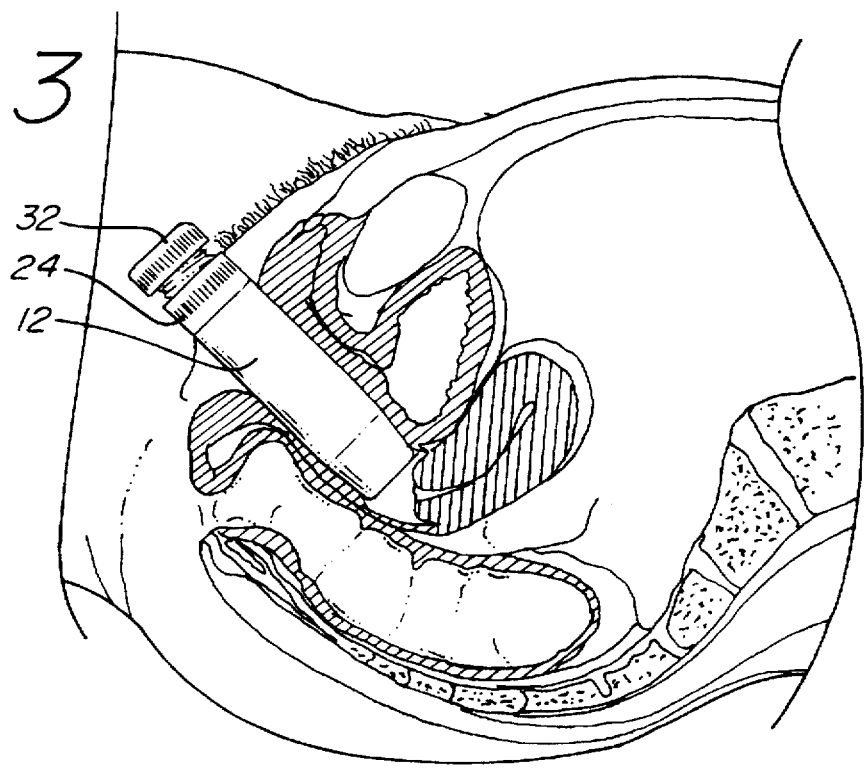
FIG. 3 is an illustration of the speculum upon expansion within the vagina.

Referring now to the drawings, it is seen that the speculum of the present invention, generally denoted by reference numeral 10, is comprised of a elongate, generally cylindrical shaft member 12 having an internal cavity passing therethrough. As seen, the shaft member 12 has a proximal end 14 and a distal end 16. If desired, the distal end 16 of the shaft member 12 may be tapered for easier insertion into the female vagina. The shaft member 12 has an outer layer 18 and an inner layer 20. Defined between the outer layer 18 and the inner layer 20 is a sealed bladder 22 encompassing the shaft member 12. The sealed bladder 22 may be filled with an appropriate bio-acceptable liquid such as sterile water, saline solution and the like.

The outer layer 18 and the inner layer 20 are each formed from a soft resilient material that is capable of expanding and contracting.

As seen in FIGS. 4–6, an end cap 24 is attached to the shaft member 12. The end cap 24 can be attached to the shaft member 12 in any desired fashion including the illustrated annular ring 26 of the end cap 24 disposed within the annular groove 28 of the shaft member 12. At least one elongate guide member 30 is attached to the end cap 24 and runs along the length of and within the cavity of the shaft member 12 and terminates proximate the distal end 16. Each of the at least one guide members 30 may, but need not be, attached to the inner layer 20. Each of the at least one guide members 30 is formed from a sturdy material having resilient properties. If desired, an additional layer (not illustrated) may be placed over top the at least one guide member 30) to hide the guide member 30 from view.

An expansion cap 32 is rotatably (as illustrated, threadably) received within the end cap 24. The expansion cap 32 can rotate into the end cap 24 and thus render the device 10 into an expanded position and out of the end cap 24 and thus render the device 10 into a retracted position. If desired, stop means (not illustrated) can be provided so that the expansion cap 32 is not completely discharged from the end cap 24 during outward rotation. Both the expansion cap 32 and the end cap 24 have a hollow interior portion generally aligned with the cavity of the shaft member 12. As seen, a spring 34 has one end attached to one of the guide members 30 proximate the distal end 16 of the shaft member 12 and the opposing end attached to the expansion cap 32.

Referring to FIGS. 4-6, it is seen that in a retracted position, the device 10 has the expansion cap 32 rotated relatively far out of the end cap 24 (as illustrated in FIG. 4). In this position, the spring 34 is at its maximum lateral length and thus has its maximum number of coil rotations. This results in a relatively small diameter for each coil rotation, which in turn results in a relatively small diameter for the cavity of the shaft member 12 and the shaft member 12 itself. The resilient nature of the shaft member 12 and the at least one guide member 30 permit this retraction of the device 10. As seen in FIG. 5, as the expansion cap 32 is rotated into the end cap 24, the expansion cap 32 progresses toward the distal end 16 of the shaft member 16 causing reduction in the lateral length of the spring 34 which reduces the number of coil turns of the spring 34 and thereby increases the diameter of each coil turn. The expansion of each coil turn of the spring 34 causes a like expansion of the cavity and the shaft member 12. As seen in FIG. 6, continued rotation of the expansion cap 32 into the end cap 24 causes further reduction in the lateral length of the spring 34 which further reduces the number of coil turns of the spring 34 and thereby further increases the diameter of each coil turn. The further expansion of each coil turn of the spring 34 causes a like further expansion of the cavity and the shaft member 12. Counter-rotation of the expansion cap 32 out of the end cap 24 causes reversal of the above process.

In order to utilize the speculum 10 of the present invention, the device 10 is provided in its retracted configuration as illustrated in FIG. 4. The device 10, in this retracted position, is inserted into the female vagina. The optional tapered distal end of the shaft member 12 assists in this insertion. Once the device 10 is properly inserted into the patient, the expansion cap 32 is rotated in order to cause expansion of the shaft member 12 (as illustrated in FIG. 5). Expansion cap rotation is continued until the shaft member 12 is fully expanded (as illustrated in FIG. 6). At this stage, the medical practitioner is capable of performing the vaginal-pelvic examination in the usual way. The cavity aligned with the hollow interior portions of the expansion cap 32 and the end cap 24 give the medical practitioner a clear visual line of sight into the female anatomy as well as physical access in order to perform bacterial or viral culture specimen obtainment.

Upon competition of the medical examination, the expansion cap 32 is counter-rotated in order to reverse the above articulating process and thus reduce cavity and shaft member 12 diameter. Once accomplished, the device 10 is removed from the female patient.

In order to increase comfort to the female patient, the bladder 22 is filled with the appropriate liquid solution. The liquid within the bladder 22 gives the shaft member 12 a soft water-bed-like quality that reduces physical anxiety associated with the device 10. The liquid can be placed into the bladder at initial device 10 manufacture and shipped therein. In such an embodiment, appropriate means can be utilized in order to heat the contained liquid prior to usage. The heated liquid can be at temperature that approximates that of the human body which increases physical comfort to the female patient during device 10 usage.

Alternately, a threaded end 36 with valve, of any appropriate design known in the art, can be provided in order to introduce liquid into the bladder 22 via a conduit 38 as desired. In such a design, the liquid can be preheated prior to introduction into the device 10, or the liquid can be heated after insertion into the device 10.

While the invention has been particularly shown and described with reference to an embodiment thereof, it will be appreciated by those skilled in the art that various changes in form and detail may be made without departing from the spirit and scope of the invention.

I claim:

1. A speculum comprising:

a generally elongate shaft, having a proximal end, a distal end, an outer surface, and an inner surface delimiting a central cavity, the shaft member capable of articulating between a retracted position wherein the cavity has a first diameter to an expanded position wherein the cavity has a second diameter that is greater than the first diameter;

an end cap, having a first hollow central portion, attached to the shaft proximate the proximal end, such that the first hollow central portion is generally aligned with the cavity;

at least one elongate guide member having a first end attached to the end cap and a second end terminating proximate the distal end, disposed within the cavity;

an expansion cap, having a second hollow central portion, rotatably disposed within the end cap such that the second hollow central portion is generally aligned with the first hollow central portion and such that rotation of the expansion cap causes the expansion cap to rotate into the end cap and counter-rotation of the expansion cap causes the expansion cap to rotate out of the end cap; and a spring having a third end attached to the expansion cap and a fourth end attached to the second end of one of the at least one guide member.

2. The speculum as in claim 1 wherein each of the at least one guide member is constructed from a resilient material.

3. The speculum as in claim 1 wherein the distal end is tapered.

4. The speculum as in claim 1 wherein the outer surface encompasses a bladder.

5. The speculum as in claim 4 further comprising a fill means for filling the bladder with the liquid.

6. The speculum as in claim 5 wherein the fill means comprises:

a valve, adapted to receive a liquid stream therethrough; and a conduit for liquid flow connecting the valve and the bladder.

* * * * *